United States Patent [19]

Lewis et al.

[11] Patent Number: 5,554,627
[45] Date of Patent: Sep. 10, 1996

[54] TACHYKININ ANTAGONISTS

[75] Inventors: Richard T. Lewis, Harlow; Angus M. MacLeod; Kevin J. Merchant, both of Bishops Stortford, all of United Kingdom

[73] Assignee: Merck, Sharp & Dohme Ltd., Hoddesdon, England

[21] Appl. No.: 428,065

[22] PCT Filed: Oct. 27, 1993

[86] PCT No.: PCT/GB93/02213

§ 371 Date: Apr. 27, 1995

§ 102(e) Date: Apr. 27, 1995

[87] PCT Pub. No.: WO94/10167

PCT Pub. Date: May 11, 1994

[30]  Foreign Application Priority Data

Oct. 30, 1992 [GB] United Kingdom ............... 9222820
Nov. 17, 1992 [GB] United Kingdom ............... 9224098
Dec. 14, 1992 [GB] United Kingdom ............... 9226057
Mar. 23, 1993 [GB] United Kingdom ............... 9306031

[51] Int. Cl.⁶ .................. A61K 31/445; C07D 453/00
[52] U.S. Cl. .................. 514/305; 514/339; 514/419; 544/143; 544/238; 540/585; 546/133; 546/201; 546/14; 546/277.4; 548/127; 548/128; 548/181; 548/213; 548/214; 548/217; 548/235; 548/247; 548/253; 548/267.2; 548/305.1; 548/312.1
[58] Field of Search .................. 546/273, 133, 546/201; 548/496, 127, 128, 181, 213, 214, 217, 235, 247, 253, 267.2, 305.1, 312.1, 455; 514/339, 419; 540/585; 544/143, 238

[56]  References Cited

U.S. PATENT DOCUMENTS 4,853,376  8/1989  King ........................... 514/161
5,187,156  2/1993  Matsuo ......................... 214/18
5,256,671  10/1993  Ladduwhetty ................. 514/305

FOREIGN PATENT DOCUMENTS

0333174A3  3/1989  European Pat. Off. .
0394989A3  4/1990  European Pat. Off. .
WO93/18023  9/1993  WIPO .
T1194Y/WO  1/1994  WIPO .

OTHER PUBLICATIONS

Maggi, C. A.; et al. J. Autonom. Pharmacol (1993), 13, 23–93.
March, J. Advanced Organic Chemistry, Wiley Interscience Publications, (1992), 4th ed, p. 903.
Longmore, J. et al. "Neurokinin Receptors" DN&P8(1), Feb. 1995, pp. 5–23.

Primary Examiner—C. Warren Ivy
Assistant Examiner—Garth M. Dahlen
Attorney, Agent, or Firm—Robert J. North; Melvin Winokur

[57]  ABSTRACT

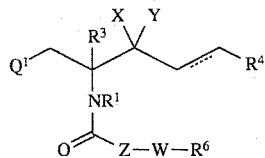

Compounds of formula (I), wherein $Q^1$ represents an aryl group; the dotted line represents an optional covalent bond; one of X and Y represents H and the other represents hydroxy or $C_{1-6}$alkoxy, or X and Y together form a group =O or =NOR⁵ where $R^5$ is H or $C_{1-6}$alkyl; Z represents O, S or NR², where $R^2$ is H or $C_{1-6}$alkyl; W represents a bond or a saturated or unsaturated hydrocarbon chain of 1, 2, 3, 4, 5 or 6 carbon atoms; $R^1$ represents H or $C_{1-6}$alkyl. $R^3$ represents H, $C_{1-6}$alkyl or $C_{2-6}$alkenyl; $R^4$ represents an optionally substituted phenyl group; and $R^6$ represents a specified amino group or an optionally substituted aromatic or non-aromatic azacyclic or azabicyclic group; and salts and prodrugs are tachykinin receptor antagonists.

11 Claims, No Drawings

TACHYKININ ANTAGONISTS

This is the national stage application of PCT/GB93/02213 filed 27 Oct. 1993.

This invention relates to a class of compounds containing carbamate, thiocarbamate or urea functionality which are useful as tachykinin receptor antagonists.

The tachykinins are a group of naturally-occurring peptides found widely distributed throughout mammalian tissues, both within the central nervous system and in the peripheral nervous and circulatory systems. The three known mammalian tachykinins are: substance P, neurokinin A and neurokinin B:

Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], and as anticonvulsants [Garant et al., Brain Research (1986) 382 372–8]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

We have now found a class of non-peptides which are potent antagonists of tachykinins.

European patent applications nos. 0394989 and 0482539 disclose tachykinin receptor antagonists comprising an indolyl or like moiety. The compounds are structurally remote from those of the present invention.

The present invention provides a compound of formula (I), or a salt or prodrug thereof:

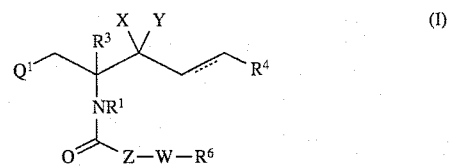

wherein $Q^1$ represents a phenyl group substituted by one or more halo, optionally substituted naphthyl, optionally substituted indolyl, optionally substituted benzthiophenyl, optionally substituted benzofuranyl, optionally substituted benzyl or optionally substituted fluorenyl;

the dotted line represents an optional covalent bond;

one of X and Y represents H and the other represents hydroxy or $C_{1-6}$alkoxy, or X and Y together form a group =O or =NOR$^5$ where R$^5$ is H or $C_{1-6}$alkyl;

Z represents O, S or NR$^2$, where R$^2$ is H or $C_{1-6}$alkyl;

W represents a bond or a saturated or unsaturated hydrocarbon chain of 1, 2, 3, 4, 5 or 6 carbon atoms;

$R^1$ represents H or $C_{1-6}$alkyl.

$R^3$ represents H, $C_{1-6}$alkyl or $C_{2-6}$alkenyl;

$R^4$ represents phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl; and $R^6$ represents $NR^7R^8$ (where $R^7$ and $R^8$ each independently represent H, $C_{1-6}$alkyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl) or an optionally substituted aromatic or non-aromatic azacyclic or azabicyclic group.

For the avoidance of doubt, when the covalent bond represented by the dotted line is present, the compounds of formula (I) contain an olefinic double bond.

The alkyl, alkenyl and alkynyl groups referred to with respect to any of the above formulae may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

As used herein, the definition of each expression, when it occurs more than once in any structure, is intended to be independent of its definition elsewhere in the same structure.

A subgroup of compounds according to the invention is represented by compounds of formula (I) wherein W represents alkyl, for example $(CH_2)_q$, where q is 0, 1, 2, 3, 4, 5 or 6.

Within this subgroup of compounds of the invention there may be identified a further subgroup of compounds of formula (I) wherein $R^6$ represents an optionally substituted aromatic or non-aromatic azacyclic or azabicyclic group.

Where $Q^1$ represents optionally substituted fluorenyl, the group is linked through the bridgehead carbon atom, that is to say, C-9.

Where $Q^1$ represents optionally substituted naphthyl, indolyl, benzothiophenyl, benzofuranyl, benzyl or fluorenyl, suitable substituents include $C_{1-6}$ alkyl, $C_{2-6}$ alkenyl, $C_{2-6}$ alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined. One or more substituents may be present and each may be located at any available ring position, except, where $Q^1$ is optionally substituted indolyl, the nitrogen atom. Where $Q^1$ is optionally substituted indolyl, suitable nitrogen substituents include $C_{1-6}$alkyl, optionally substituted phenyl($C_{1-4}$alkyl), $COOR^a$ or $CONR^aR^b$, wherein $R^a$ and $R^b$ are as above defined.

Suitable values of the group $Q^1$ include dichlorophenyl, indolyl, naphthyl, fluorenyl, benzyl, benzothiophenyl and benzofuranyl, such as 3,4-dichlorophenyl, 3-indolyl, 2-naphthyl, 3-naphthyl, 9-fluorenyl, benzyl, 3-benzothiophenyl and 3-benzofuranyl.

Preferably $Q^1$ is 3-indolyl, 3-benzothiophenyl or 3,4-dichlorophenyl, more preferably 3-indolyl.

Preferably the double bond is absent.

Suitably one of X and Y represents hydroxy or $C_{1-6}$alkoxy, such as methoxy, or X and Y together represent =O. More preferably X and Y together represent =O.

Preferably Z represents O, NH or $NCH_3$.

Preferably $R^1$ is H.

Preferably $R^3$ represents H or methyl, more preferably H.

Suitably W represents a bond or a saturated or unsaturated hydrocarbon chain of 1, 2, 3 or 4 carbon atoms, e.g. $CH_2$, $CH_2CH_2$, CH=CH, $CH_2CH_2CH_2$ or $CH_2CH_2CH_2CH_2$.

When $R^6$ represents $NR^7R^8$, $R^7$ and $R^8$ are preferably both $C_{1-6}$alkyl such as methyl, ethyl, n-propyl, i-propyl, n-butyl, i-butyl or t-butyl. More preferably $R^7$ and $R^8$ will both represent methyl.

When $R^6$ represents an aromatic or non-aromatic azacycle or azabicycle it may contain one or more (for example one or two) additional heteroatoms selected from O, S and N or groups $NR^9$, where $R^9$ is H, $C_{1-6}$alkyl or phenyl$C_{1-4}$alkyl, and may be unsubstituted or substituted. Suitable substituents include $C_{1-6}$alkyl, $C_{1-6}$alkoxy, oxo, SH, =S, halo, trifluoromethyl, $NR^aR^b$, $NR^aCOR^b$, $CONR^aR^b$, $CO_2R^a$ and $CH_2OR^a$, where $R^a$ and $R^b$ are as previously defined. Aptly $R^6$ is an aromatic azacycle of 5 or 6 ring atoms. Aptly $R^6$ is an azabicycle wherein one ring contains 5 or 6 ring atoms and the other ring contains 6 ring atoms.

When $R^6$ represents an aromatic azacycle or azabicycle, suitable values of $R^6$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl, more preferably pyridyl such as 4-, 3- or 2-pyridyl.

When $R^6$ represents a non-aromatic azacycle or azabicycle, suitable values of $R^6$ include morpholinyl, piperdinyl, pyrrolidinyl, piperazinyl, methylpiperazinyl, azanorbornanyl, 3,4-pyridinecarboximido, azabicyclo[2.2.2]octanyl and azabicyclo[3.2.2]nonyl, preferably morpholinyl, piperazinyl, methylpiperazinyl, piperidinyl, pyrrolidinyl, 3,4-pyridinecarboximido, quinuclidinyl (azabicyclo[2.2.2]octanyl), azabicyclo[2.2.1]heptanyl, azabicyclo[3.2.1]octanyl or azabicyclo[3.2.2]nonyl, more preferably quinuclidinyl. Aptly non-aromatic azacycles or azabicycles contain only one heteroatom and from 5 to 6 carbon atoms.

One subgroup of compounds according to the invention is represented by compounds of formula (I) wherein $R^6$ represents an optionally substituted aromatic or non-aromatic azacyclic or azacyclic group.

A preferred subgroup of compounds according to the invention is represented by compounds of formula (I) wherein W represents a saturated or unsaturated hydrocarbon chain and $R^6$ is pyridyl or $NR^7R^8$ wherein $R^7$ and $R^8$ each represent $C_{1-6}$alkyl, preferably $C_{1-4}$alkyl, more preferably methyl.

A further preferred subgroup of compounds according to the invention is represented by compounds of formula (I) wherein $R^6$ is N-substituted piperidinyl or quinuclidinyl, and salts thereof.

Preferably $R^4$ represents substituted phenyl. Suitable phenyl substituents include nitro, trifluoromethyl, trimethylsilyl, bromo, chloro, fluoro, iodo, cyano, methyl, ethyl, cyclopropyl, vinyl, methoxy, phenoxy and amino. Suitably $R^4$ represents monosubstituted phenyl, such as 3-substituted phenyl, or, preferably disubstituted phenyl, such as 3,5-disubstituted phenyl. Preferably $R^4$ represents phenyl substituted by 1 or 2 groups selected from $C_{1-6}$alkyl, $C_{1-6}$alkoxy, halo and trifluoromethyl.

Particularly preferred are compounds wherein $R^4$ represents 3,5-bis(trifluoromethyl)phenyl.

A particular subgroup of compounds according to the invention is represented by compounds of formula (Ia), and salts and prodrugs thereof:

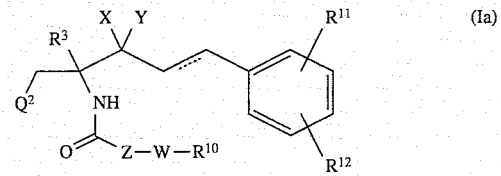

(Ia)

wherein $Q^2$ represents 3,4-dichlorophenyl or a group

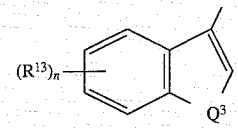

where $Q^3$ represents O, S or $NR^{14}$ (where $R^{14}$ is H, $C_{1-6}$alkyl, optionally substituted phenyl($C_{1-4}$alkyl), $CO_2R^a$ or $CONR^aR^b$, where $R^a$ and $R^b$ are as previously defined), preferably S or NH;

each $R^{13}$ may occupy any available carbon atom of the bicyclic ring system and independently represents $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined; and n is 0, 1, 2 or 3, preferably 0;

X, Y, Z and W are as defined for formula (I);

the dotted line represents an optional covalent bond;

$R^{10}$ is imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl, indolyl, morpholinyl, piperdinyl, pyrrolidinyl, 3,4-pyridinecarboximido piperazinyl, methylpiperazinyl, azanorboranyl, azabicyclo[2.2.2]octanyl or azabicyclo[3.2.2]nonyl, preferably imidazolyl, pyridyl, morpholinyl, methylpiperazinyl, quinuclidinyl, methylquinuclidinyl or azabicyclo[3.2.2]nonyl, preferably 3-pyridyl, 4-pyridyl, quinuclidinyl or methylquinuclidinyl; and $R^{11}$ and $R^{12}$ each independently represent H, $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined.

Preferred are compounds of formula (Ia) wherein the optional covalent bond is absent.

A further subgroup of compounds according to the invention is represented by compounds of formula (Ib), and salts and prodrugs thereof:

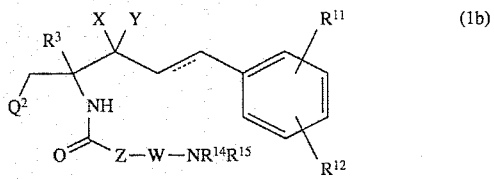

wherein $Q^2$, $R^3$, $R^{11}$, $R^{12}$, W, X, Y and Z are as previously defined;

the dotted line represents an optional covalent bond; and $R^{14}$ and $R^{15}$ each independently represent H or $C_{1-6}$alkyl, preferably $C_{1-4}$alkyl, more preferably methyl.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when $R^6$ represents $NR^7R^8$ where $R^7$ and $R^8$ each represents other than H, or $R^6$ represents a non-aromatic heterocycle such as, for example, quinuclidinyl, the nitrogen atom may be substituted to give a quaternary ammonium salt. Such quaternary salts may be prepared by treating an appropriate compound of formula (I) with an alkylating agent, such as an alkyl halide, for example, methyl iodide. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The substance P antagonising activity of the compounds described herein was evaluated using the human NK1R assay described in published European patent application no. 0 528 495. The method essentially involves determining the concentration of the test compound required to reduce by 50% the amount of radiolabelled substance P binding to human NK1R, thereby affording an $IC_{50}$ value for the test compound. The compounds of the Examples were found to have $IC_{50}$ values less than 100 nM.

The invention also provides pharmaceutical compositions comprising one or more compounds of this invention in association with a pharmaceutically acceptable carrier. Preferably these compositions, which contain an effective amount, are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention for example 1 to 100 mg. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention luther provides a process for the preparation of a pharmaceutical composition comprising a compound of formula (I), which process comprises bringing a Compound of formula (I) into association with a pharmaceutically acceptable carrier or excipient.

The compounds of formula (I) and their pharmaceutically acceptable salts are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotropic lateral sclerosis (ALS; Lou Gehrig's disease) and other neuropathological disorders such as peripheral neuropathy, for example, diabetic or chemotherapy-induced neuropathy, and postherpetic and other neuralgias; small cell carcinoma such as small cell lung cancer; respiratory diseases such as chronic obstructive airways disease, bronchopneumonia, bronchospasm and asthma; inflammatory diseases such as inflammatory bowel disease, irritable bowel syndrome, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like, and proliferative vitreoretinopathy; cutaneous diseases such as contact dermatitis, atropic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute delayed and anticipatory emesis, for example, induced by chemotherapy, radiation, toxins, pregnancy, vestibular disorders, surgery, migraine and variations in intercranial pressure (except quaternary salts); disorders of bladder function such as cystitis and bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine. The compounds of formula (I) and their pharmaceutically acceptable acid addition salts are also particularly useful for the treatment of emesis.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a pharmaceutically acceptable salt therof or a composition comprising a compound of formula (I) or a pharmaceutically acceptable salt therof.

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykininantagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day (the kg refers to patient weight). For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

Compounds of formula (I) may be prepared by reaction of intermediates of formula (II) with compounds of formula (III):

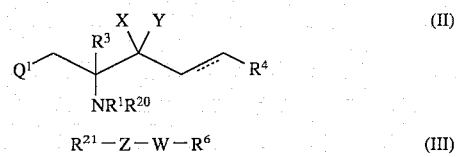

$$R^{21}-Z-W-R^6 \quad (III)$$

wherein $Q^1$, $R^3$, $R^4$, $R^6$, W, X, Y, Z and—are as defined for formula (I), and one of $R^{20}$ and $R^{21}$ represents a group CO—A, where h represents an activating group, and the other of $R^{20}$ and $R^{21}$ represents H, in the presence of a base.

Suitable activating groups represented by A include phenoxy substituted by one or more electron-withdrawing substituents. A preferred activating group is 4-nitrophenoxy.

Suitable bases of use in the reaction include tertiary amines such as, for example, triethylamine, or dimethylaminopyridine (DMAP).

When Z represents $NR^2$, $R^{20}$ preferably represents CO—A and $R^{21}$ preferably represents H.

When Z represents O or S, $R^{20}$ preferably represents H and $R^{21}$ preferably represents CO—A.

Alternatively, compounds of formula (I) wherein Z is NH may be prepared from intermediates of formula (II) wherein $R^{20}$ is H (hereinafter intermediates (IIA)) by reaction with an isocyanate of formula $R^6$—W—N=C=O.

The reaction is conveniently effected in a suitable organic solvent such as an ether, for example, tetrahydrofuran.

Compounds of formula (II) wherein $R^{20}$ is an activating group may be prepared from corresponding intermediates (IIA) by reaction with a compound of formula (IV)

wherein A represents an activating group, such as a phenyl group bearing one or more electron-withdrawing substituents, for example, 4-nitrophenyl, and Hal represents halo, such as chloro or bromo, in the presence of a base.

Suitable bases of use in the reaction include tertiary amines, such as, for example, triethylamine.

Compounds of formula (III) wherein $R^{21}$ is an activating group may be prepared from corresponding compounds of formula (III) wherein $R^{21}$ is H, by reaction with a compound of formula (IV) in the presence of a base, such as a tertiary amine, for example, triethylamine or DMAP.

Intermediates of formula (II) wherein $R^{20}$ is H, X and Y together represent =O and the double bond is present may be prepared by reaction of an aldehyde of formula $R^4CHO$ with a compound of formula (V):

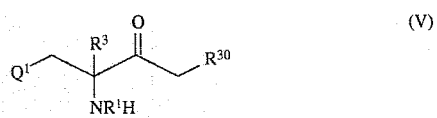

wherein $Q^1$, $R^1$ and $R^3$ are as defined for formula (I) and $R^{30}$ represents a group $PR^x_3$ or $PO(OR^x)_2$, wherein $R^x$ represents phenyl or $C_{1-10}$alkyl, in the presence of a base.

Suitable bases include alkali metal hydrides, such as, for example, sodium hydride, alkali metal carbonates, such as, for example, potassium carbonate, alkali metal carbonates, such as, for example, potassium carbonate, and strong organic bases such as, for example, 1,8-diazabicylo[5.4.0]undec-7-ene in the presence of anhydrous lithium chloride.

The reaction is conveniently effected in a suitable organic solvent, such as an ether, e.g. tetrahydrofuran, or acetonitrile, suitably at ambient temperature.

Compounds of formula (II) wherein one of X and Y represents H and the other represents hydroxy may be prepared from the corresponding compounds of formula (II) wherein X and Y together represent =O, by reduction.

Suitable reducing agents include, for example, hydride reducing agents such as lithium aluminium hydride and sodium borohydride.

The reaction is conveniently carried out in a suitable organic solvent, such as an ether, e.g. tetrahydrofuran, suitably at ambient temperature.

Compounds of formula (II) wherein one of X and Y represents H and the other represents $C_{1-6}$alkoxy may be prepared from the corresponding compounds of formula (II) wherein one of X and Y represents H and the other represents hydroxy, by alkylation.

Suitable alkylation procedures include treatment of an alcohol of formula (II) with an alkali metal hydride, such as sodium hydride, and a $C_{1-6}$alkylhalide. Suitable halides include, in particular, bromides and iodides.

The reaction is conveniently effected in an anhydrous organic solvent, for example, an ether, e.g. dimethoxyethane, suitably at ambient temperature.

Compounds of formula (II) wherein X and Y together represent =NOR$^5$ may be prepared from the corresponding compounds of formula (II) wherein X and Y together represent =O by the addition of hydroxylamine, or a derivative thereof. Compounds wherein $R^5$ is other than H may be prepared from the corresponding compounds wherein $R^5$ is H by alkylation, for example, using a diazo compound, such as diazomethane, or an alkyl halide or sulphate.

Compounds of formula (II) wherein the double bond is absent may be prepared from the corresponding unsaturated compounds of formula (II) by reduction.

Suitable reduction procedures include catalytic hydrogenation. Suitable hydrogenation catalysts include nobel metals, for example, platinum or palladium, or oxides thereof, which may be supported, for example, on charcoal. A preferred catalyst is Wilkinson's catalyst (tris(triphenylphosphine)rhodium(I)chloride).

The reaction is conveniently effected in a suitable organic solvent, such as an ether, e.g. tetrahydrofuran, an alcohol, e.g. ethanol, or an ester, e.g. ethyl acetate, suitably at ambient temperature.

Compounds of formula (III) wherein $R^{21}$ is H are commercially available or may be prepared from commerically available starting materials by conventional procedures well-known to those skilled in the art.

Compounds of formula (V) may be prepared from compounds of formula (VI)

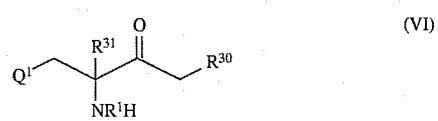

wherein $Q^1$, $R^1$ and $R^3$ are as defined for formula (I) and $R^{31}$ represents an alkoxy or a suitably substituted amino group, such as a group $NR^yOR^z$, where $R^y$ and $R^z$ represent alkyl, in particular a group $NCH_3(OCH_3)$, by reaction with a compound of formula $CH_3PO(OR^x)_2$, where $R^x$ is an alkyl group, in the presence of a base.

Suitable reaction procedures will be readily apparent to the skilled person and examples thereof are described in the accompanying Examples.

Suitable bases of use in the reaction include alkyl lithiums, such as butyl lithiums.

Compounds of formula (VI) are commercially available or may be prepared using standard procedures well known to the skilled person in the art. The compounds of formula (IV) are amino acid derivatives. Syntheses of amino acids and derivatives thereof are well documented and are described, for example, in *Chemistry and Biochemistry of the Amino Acids*, ed. G. C. Barrett, Chapman and Hall, 1985.

Where the above-described processes for the preparation of the compounds according to the invention give rise to mixtures of stereoisomers, these isomers may be separated, suitably by conventional techniques such as preparative chromatography:

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

Using test methods described in PCT/GB92/01212 (International Publication No. WO 93/01159) pages 30–33, it was found that the compounds referred to in the Examples hereinafter had $IC_{50}$ at NKIR of less than 50 nM. The following illustrate pharmaceutical compositions according to the invention.

|  | Amount mg | | |
|---|---|---|---|
| Tablets containing 1–25 mg of compound | | | |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |
| Tablets containing 26–100 mg of compound | | | |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

| Parenteral injection | |
|---|---|
|  | Amount mg |
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

| Topical formulation | |
|---|---|
|  | Amount mg |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

The following non-limiting Examples illustrate the preparation of compounds according to the invention.

EXAMPLE 1

5-(3,5-Bis(trifluoromethyl)phenyl)-1-(3-indolyl)-2-(4-pyridyl methoxycarbonylamino)-3-pentanone (a) N-Methoxy, N-methyl 2-t-butyloxycarbonylamino-3-(3-indolyl) propionamide N-α-BOC-L-tryptophan (100 g) was dissolved in dimethyl formamide (800 ml) and triethylamine (101 g) was added. The reaction was cooled to −30° C. and isobutyl chloroformate (42.5 ml) was added, maintaining the internal temperature to below −20° C. The reaction was stirred for 15 minutes before adding N,O-dimethyl hydroxylamine hydrochloride (64 g) and then diluting the reaction with dichloromethane (1 l), maintaining the internal temperature below 0° C. The reaction was stirred for 15 minutes, poured into ethyl acetate (3 l) and washed with 10% citric acid (1 l), water (3×1 l), saturated sodium bicarbonate (1 l) and water (1 l). The organic phase was dried ($MgSO_4$), filtered, and evaporated until crystallisation ensued. The suspension was diluted with petroleum ether, filtered and dried to yield the title compound; mp=129°–130° C.; $^1$H NMR(360 MHz, $D_6DMSO$)δ10.80(1H, s); 7.51 (1H, d, J=7 Hz); 7.33 (1H, d, J=7 Hz); 7.16 (1H, s); 7.08–6.97 (3H, m); 4.62–4.58 (1H, m); 3.72 (3H, s); 3.34 (3H, s); 3.02–2.81 (2H, m); 1.31 (9H, s).

(b) 2-t-Butyloxycarbonylamino-1-(3-indolyl)-4-dimethylphosphone-3-butanone

Dimethyl methane phosphonate (205 g) was dissolved in tetrahydrofuran (800 ml), cooled to −70° C.; and then treated with n-butyllithium (1.6M in hexane, 900 ml ), maintaining the internal temperature of the reaction at below −55° C. The reaction was stirred for one hour before adding the product of part (a) (90 g). The reaction was stirred at −70° C. for 30 minutes before quenching with saturated ammonium chloride. The resulting mixture was extracted with ethyl acetate and the organic extract was washed with water (5×500 ml), dried ($MgSO_4$) and evaporated. The residue was purified on silica (eluting with ethyl acetate) to yield the title compound as an oil; $^1$H NMR (360MHz, $CDCl_3$)δ10.84 (1H, s), 7.56 (1H, d, J=7 Hz), 7.33 (1H, d, J=7 Hz), 6.98 (1H, t, J=7 Hz), 4.34–4.31 (1H, m), 3.63 (6H, d, J=11 Hz), 3.39 (2H, d, J=22 Hz), 3.19–3.11 (1H, m), 2.91–2.84 (1H, m); found: C, 55.73, H, 6.34; N, 6.80; $C_{19}H_{27}N_2O_6P$ requires C, 55.60;H, 6.63; N, 6.82%.

(c) 5-(35-Bis(trifluoromethyl)phenyl)-2-t-butyloxycarbonylamino-1-(3-indolyl)-4-penten-3-one A solution of the product of part (b) (69.0 g) in acetonitrile (600 ml) was stirred with diisopropylethylamine (43.3 g), and anhydrous lithium chloride (14.13 g) for 30 minutes before adding 3,5-bis(trifluoromethyl)benzaldehyde (55 g) in acetonitrile (200 ml). The reaction was stirred for two hours then the solvent was removed and the residue partitioned between ethyl acetate and water. The organic phase was washed with 10% citric acid (500 ml), water (500 ml), satm;ated sodium bicarbonate (500 ml) and water (500 ml). The solution was dried ($MgSO_4$), filtered and evaporated. The residue was purified by column chromatography on silica using ethyl acetate/petroleum ether (1:4) to yield the title compound as a pale yellow solid, mp=137°–138° C.; found: C, 59.23; H, 4.79; N, 5.35; $C_{26}H_{24}F_6N_2O_3$ requires C, 59.32; H, 4.60; N 5.32%.

(d) 5-(3,5-Bis(trifluoromethyl)phenyl)-2t-butyloxycarbonylamino-1-(3-indolyl)-3-pentanone The product of part (c) was heated under reflux with tri-n-butyltin hydride (51.12 g) in toluene for 20 hours. The reaction was cooled and purified by column chromatography on silica using ethyl acetate/petroleum ether (1:4) to yield the title compound as a white solid (37.1 g), mp=138°–140° C.: found: C, 59.23; H, 4.90; N, 5.28; $C_{26}H_{24}F_6N_2O_3$ a requires C, 59.09, H, 4.96; N, 5.30%.

(e) 2-Amino-5-(3,5-bis(trifluoromethyl)phenyl)-1-(3-indolyl)-3-pentanone Hydrochloride The product of part (d) was treated with ethereal hydrogen chloride for one hour. The precipitated white solid was filtered and dried, mp=84°–86° C.; found: C, 54.40; H, 4.25; N, 6.10; $C_{21}H_{18}F_6N_2O$. HCl requires C, 54.26; H, 4.12; N, 6.03%.

(f) 5-(3,5-Bis(trifluoromethyl)phenyl)-1-(3-indolyl)-2-(4-pyridylmethoxy carbonylamino)-3-pentanone To a solution of 4-nitrophenylchloroformate (0.22 g) in dichloromethane (10 ml) at 0° C. was added 4-hydroxymethylpyridine (0.12 g) and 4-dimethylaminopyridine (0.13 g). After stirring for 2 hours the solvent was removed in vacuo and the residue dissolved in dimethylfomamide (10 ml). The compound of Example 1(e) (0.5 g) and 4-dimethylaminopyridine (0.13 g) was added and the solution stirred for 16 hours then diluted with ethyl acetate and washed with water (3×). The organic solution was dried ($Na_2SO_4$) and concentrated and the residue purified by chromatography on silica gel eluting with ethyl acetate-petroleum ether (3:1). Treatment with ethereal hydrogen chloride gave the title compound, mp 95°–98° C.; found C, 53.12; H, 4.19; N, 6.81%. $C_{28}H_{23}F_6N_3O_3$. HCl. $2H_2O$ requires C, 52.88; H, 4.43; N, 6.61%.

EXAMPLE 2

5-(3,5-Bis(trifluoromethyl)phenyl)-1-(3-indolyl)-2-(3-pyridyl methoxycarbonylamino)-3-pentanone Prepared by the method of Example 1 using 3-hydroxymethylpyridine. Mp 144°–146.5° C.; found C, 52.89; H, 3.90; N, 6.51%. $C_{28}H_{23}F_6N_3O_3$.HCl.$2H_2O$ requires C, 52.87; H, 4.43; N, 6.60%.

EXAMPLE 3

5-(3,5-Bis(trifluoromethyl)phenyl)-1-(3-indolyl)-2-(3-(4-pyridylmethyl)ureido)- 3-pentanone Hydrochloride The compound of Example 1(e) (400 mg) in tetrahydrofuran (10 ml) was treated with triethylamine (0.12 ml) and 4-nitrophenylchloroformate (174 mg) for 1 hour. The solvent was removed in vacuo and the residue partitioned between ethyl acetate and water. The organic solution was dried ($Na_2SO_4$) and concentrated to give a solid which was dissolved in tetrahydrofuran (15 ml). 4-Aminomethylpyridine (0.085 ml) was added and the solution stirred for 16 hours then concentrated in vacuo. The residue was partitioned between ethyl acetate and potassium carbonate solution. The organic solution was dried ($Na_2SO_4$), concentrated and the residue treated with ethereal hydrogen chloride to give the title compound, mp 171°–174° C.; found: C, 53.94; H, 4.31; N, 8.87%. $C_{27}H_{25}F_6N_4O_2$. HCl. 1.5 $H_2O$ requires C, 53.72; H, 4.50; N, 8.95%.

EXAMPLE 4

5-(3,5-Bis(trifluoromethyl)phenyl)-1-(3-indolyl)-2-(3-(4-quinuclidinyl)ureido)-3-pentanone Hydrochloride To a suspension of quinuclidine-4-carboxylic acid (2.0 g) in tetrahydrofuran (100 ml) was added triethylamine (0.77 ml) and diphenylphosphoryl azide (2.8 g). The solution was heated under reflux for 16 hours then concentrated under reduced pressure. The residue was dissolved in dichloromethane (100 ml) and triethylamine (0.77 ml) was added followed by the compound of Example 1(e) (5.0 g). After stirring for 4 hours the reaction mixture was diluted with ethyl acetate and washed with water, then dried and concentrated. The residue was purified by chromatography on neutral alumina eluting with methanol-dichloromethane (1:9), then treatment with ethereal hydrogen chloride and crystallisation from ethyl acetate to give the title compound, mp 199°–201° C.

EXAMPLE 5

5-(3,5-Bis(trifluoromethyl)phenyl)-1-(3-indolyl)-2-(3-(4-(1-methyl)quinuclidinyl) ureido)-3-pentanone Iodide To a solution of the compound of Example 4, free base (50 mg) in acetone (1 ml) was added methyl iodide (0.1 ml). The solution was left to stand for 16 hours then evaporated and the residue recrystallised from ethyl acetate to give the title compound, mp 135°–138° C.

EXAMPLE 6

5-(3,5-Bis(trifluoromethyl)phenyl)-1-(3-indolyl)-2-(3-(4-(1-ethyl)quinuclidinyl)ureido)-3-pentanone Bromide Prepared by the method of Example 5 using ethyl bromide. Mp 237°–238° C.; found: C, 53.74; H, 5.18; N, 8.09. $C_{31}H_{35}BrF_6N_4O_2$ requires C, 54.00; H, 5.12; N, 8.13.

EXAMPLE 7

5-(3,5-Bis(trifluoromethyl)phenyl)-1-(3-indolyl)-2-(4-(1-methyl)piperidinyl)oxycarbonylamino)-3-pentanone Hydrochloride Prepared by the method of Example 1f) using 4-hydroxy-1-methylpiperidine with purification of the title compound by chromatography on neutral alumina eluting with methanoldichloromethane (1:9) followed by treatment with ethereal hydrogen chloride. Mp 215°–217° C.; found: C, 55.73; H, 4.85; N, 7.03. $C_{28}H_{29}F_6N_3O_3$.HCl requires C, 55.50; H, 5.00; N, 6.93.

EXAMPLE 8

5-(3,5-Bis(trifluoromethyl)phenyl)-1-(3-indolyl)2-(3-(4-(1-benzyl)piperidinyl)ureido)-3-pentanone Prepared by the method of Example 3 using N-benzyl-4-aminopiperidine. Mp 137°–138° C.; found: C, 62.09; H, 5.23; N, 8.50. $C_{34}H_{34}F_6N_4O_2$.$0.5H_2O$ requires C, 62.47; H, 5.39; N, 8.57.

EXAMPLE 9

5-(3,5-Bis(trifluoromethyl)phenyl)-1-(3-indolyl)-2-(4-quinuclidinyl) oxycarbonylamino)-3-pentanone Hydrochloride Prepared by the method of Example 7 using 4-hydroxymethylquinuclidine. Mp 212°–215° C.; found: C, 56.61; H, 5.03; N, 6.53. $C_{30}H_{31}F_6N_3O_3$.HCl.$0.25H_2O$ requires C, 56.61; H, 5.15; N, 6.60.

EXAMPLE 10

5-(3,5-Bis(trifluoromethyl)phenyl)-1-(3-indolyl)-2-(3-methyl-3-(dimethylaraidoethyl)ureido)-3-pentanone Prepared by the method of Example 3 using N,N,N'-trimethylethylenediamine. Mp 112°–115° C.; found: C, 58.12; H, 5.31; N, 9.94. $C_{27}H_{30}F_6N_4O_2$ requires C, 58.27; H, 5.43; N, 10.07.

EXAMPLE 11

5-(3,5-Bis(trifluoromethyl)phenyl)-1-(3-indolyl)-2-(3-methyl-3-(dimethylaminopropyl)ureido)-3-pentanone Prepared by the method of Example 3 using N,N,N'-trimethyl-1,3-propanediamide. Mp 135°–137° C.; found: C, 58.91; H, 5.54; N, 9.57. $C_{28}H_{32}F_6N_4O_2$ requires C, 58.94; H, 5.65; N, 9.81.

EXAMPLE 12

5-(3,5-Bis(trifluoromethyl)phenyl)-1-(3-indolyl)-2-(diethylaminopropyloxy carbonylamino)-3-pentanone Prepared by the method of Example 1f) using 3-N,N-dimethylamino-1-propanol. Mp 110°–115° C.; found: C, 59.03; H, 5.30; N, 7.45. $C_{27}H_{29}F_6N_3O_3$ requires C, 59.16; H, 5.24; N, 7.53.

EXAMPLE 13

5-(3,5-Bis(trifluoromethyl)phenyl)-1-(3-indolyl)-2-((2-pyridyl)ethoxycarbonylamino)-3-pentanone Prepared by the method of Example 1f) using 2-hydroxyethylpyridine. Mp 133°–135° C.; found: C, 59.73; H, 4.21; N, 7.00. $C_{29}H_{25}F_6N_3O_3.0.25H_2O$ requires C, 59.85; H, 4.42; N, 7.22.

EXAMPLE 14

5-(3,5-Bis(trifluoromethyl)phenyl)-1-(3-indolyl)-2-(3-methyl-3-(2-(4-pyridyl)ethyl)ureido)-3-pentanone a) N-Methyl-N-(2-(4-pyridyl)ethyl)amine Ethyl-4-pyridylacetate (2 g) was allowed to stand in methanol (50 ml), saturated with methylamine gas, for 3 days. The solution was evaporated under reduced pressure and the residue heated under reflux for 16 hours in toluene (20 ml) with boranedimethylsulphide complex (1.26 ml). The solution was cooled then treated with methanol (1.5 ml) for 1 hour. Hydrogen chloride gas was bubbled through the solution until the pH was less than 2. The solution was heated under reflux for 1 hour then cooled and concentrated. Aqueous sodium hydroxide was added and the mixture extracted with ethyl acetate. The ethyl acetate solution was dried ($Na_2SO_4$) and evaporated under reduced pressure to give the title compound as a yellow oil.

b) 5-(3,5-Bis(trifluoromethyl)phenyl)-1-(3-indolyl)2-(3-methyl-3-(2-(4-pyridyl)ethyl)ureido)-3-pentanone Prepared by the method of Example 3 using the compound of Example 14a). Mp 79°–81° C.; found: C, 60.76; H, 4.68; N, 9.40. $C_{30}H_{28}F_6N_4O_2$ requires C, 61.01; H, 4.78; N, 9.49.

EXAMPLE 15

5-(3,5-Bis(trifluoromethyl)phenyl)-1-(3-indolyl)-2-(3-(4-(1-(2-chloro)ethyl)quiniuclidinyl) ureido)-3-pentanone Chloride The compound of Example 4 was heated under reflux in 1,2-dichloroethane for 24 hours. The solvent was evaporated under reduced pressure and the residue crystallised from ethyl acetate to give the title compound, mp 247° C.; found: C, 53.09; H, 4.84; N, 7.93.$C_{31}H_{34}Cl_2F_6N_4O_2.H_2O$ requires C, 53.38; H, 5.20; N, 8.02.

We claim:

1. A compound of formula (I), or a salt or prodrug thereof:

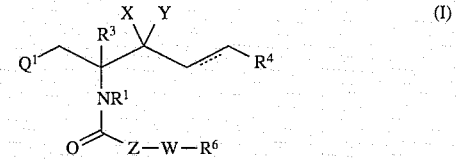

wherein $Q^1$ represents unsubstituted indolyl or indolyl substituted by one or more substituents selected from carbon atom substituents of the group consisting of $C_{1-6}$alkyl, $C_{2-6}$alkenyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$ and nitrogen atom substituents of the group consisting of $C_{1-6}$alkyl, phenyl($C_{1-4}$alkyl), substituted phenyl($C_{1-4}$alkyl) wherein the substituents are one or more carbon atom substituents, as previously defined, $COOR^a$ or $CONR^aR^b$, where $R^a$ and $R^b$ independently represent H, $C_{1-6}$alkyl, phenyl or trifluoromethyl;

the dotted line represents an optional covalent bond;

one of X and Y represents H and the other represents hydroxy or $C_{1-6}$alkoxy, or X and Y together form a group =O or =$NOR^5$ where $R^5$ is H or $C_{1-6}$alkyl;

Z represents O, S or $NR^2$, where $R^2$ is H or $C_{1-6}$alkyl;

W represents a bond or a saturated or unsaturated hydrocarbon chain of 1, 2, 3, 4, 5 or 6 carbon atoms;

$R^1$ represents H or $C_{1-6}$alkyl;

$R^3$ represents H, $C_{1-6}$alkyl or $C_{2-6}$alkenyl;

$R^4$ represents phenyl optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$, or $CONR^aR^b$, where $R^a$ and $R^b$ independently represent H, $C_{1-6}$alkyl, phenyl or trifluoromethyl; and $R^6$ represents $NR^7R^8$ (where $R^7$ and $R^8$ each independently represent H, $C_{1-6}$alkyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl) or an optionally substituted aromatic or non-aromatic azacyclic or azabicyclic group.

2. A compound as claimed in claim 1 wherein $R^6$ is an optionally substituted aromatic or non-aromatic azacyclic or azabicyclic group and Z is a —$(CH_2)_q$-group.

3. A compound as claimed in claim 1 wherein $R^3$ is H, X and Y together represent =O and the double bond is absent.

4. A compound as claimed in claim 1 wherein $Q^1$ is an 3-indolyl group.

5. A compound as claimed in claim 1 wherein $R^1$ is H and Z is O, NH or $NCH_3$.

6. A compound as claimed in claim 1 wherein $R^4$ is 3,5-bis(trifluoromethyl)phenyl.

7. A compound as claimed in claim 1 wherein q is 0, 1 or 2 and $R^6$ is 3-pyridyl, 4-pyridyl, quinuclidinyl or methylquinuclidinyl.

8. A compound which is:

5-(3,5-(bistrifluoromethyl)phenyl)-1-(3-indolyl)-2-(4-pyridylmethoxycarbonylamino)- 3-pentanone;

5-(3,5-bis(trifluoromethyl)phenyl)-1-(3-indolyl)-2-(3-pyridylmethoxycarbonylamino)- 3-pentanone;

5-(3,5-bis(trifluoromethyl)phenyl)-1-(3-indolyl)-2-(4-pyridylmethylureido)- 3-pentanone hydrochloride;

5-(3,5-bis(trifluoromethyl)phenyl)-1-(3-indolyl)-2-(3-(4-quinuclidinyl)ureido)-3-pentanone hydrochloride;

5-(3,5-bis(trifluoromethyl)phenyl)-1-(3-indolyl)-2-(3(4-(1-methyl)quinuclidinyl)ureido)-3-pentanone iodide;

5-(3,5-bis(trifluoromethyl)phenyl)-1-(3-indolyl)-2-(3-(4-(1-ethyl)quinuclidinyl)ureido)-3-pentanone bromide;

5-(3,5-bis(trifluoromethyl)phenyl)-1-(3-indolyl)-2-(4-(1-methyl)piperidinyl)oxycarbonylamino)-3-pentanone hydrochloride;

5-(3,5-bis(trifluoromethyl)phenyl)-1-(3-indolyl)-2-(3-(4-(1-benzyl)piperidinyl)ureido)- 3-pentanone;

5-(3,5-bis(trifluoromethyl)phenyl)-1-(3-indolyl)-2-(4-quinuclidinyl)oxycarbonylamino)- 3-pentanone hydrochloride;

5-(3,5-bis(trifluoromethyl)phenyl)-1-(3-indolyl)-2-(3-methyl- 3-(dimethylaminoethyl)ureido)-3-pentanone;

5-(3,5-bis(trifluoromethyl)phenyl)-1-(3-indolyl)-2-(3-methyl- 3-(dimethylaminopropyl)ureido)-3-pentanone;

5-(3,5-bis(trifluoromethyl)phenyl)-1-(3-indolyl)- 2-(dimethylaminopropyloxycarbonylamino)- 3-pentanone;

5-(3,5-bis(trifluoromethyl)phenyl)-1-(3-indolyl)-2-((2-pyridyl)ethoxycarbonylamino)- 3-pentanone;

5-(3,5-bis(trifluoromethyl)phenyl)-1-(3-indolyl)-2-(3-methyl- 3-(2-(4-pyridyl)ethyl)ureido)-3-pentanone;

5-(3,5-bis(trifluoromethyl)phenyl)-1-(3-indolyl)-2-(3-(4-(1-(2-chloro)ethyl)quinuclidinyl)ureido-3-pentanone chloride;

or a pharmaceutically acceptable salt thereof.

9. A pharmaceutical composition which comprises a compound as claimed in claim 1 and a pharmaceutically acceptable carrier thereof.

10. A method of treatment of a clinical condition caused by the presence of an excess of tachykinin which comprises administering to the patient in need thereof an effective amount of a compound as claimed in claim 1.

11. The method of claim 10 wherein said clinical condition is selected from pain, inflammation, migraine or emesis.

* * * * *